(12) United States Patent
Fischer et al.

(10) Patent No.: US 7,196,195 B2
(45) Date of Patent: Mar. 27, 2007

(54) DESLORATADINE SALTS, PROCESS FOR THEIR SYNTHESIS AND PHARMACEUTICAL COMPOSITIONS THEREOF

(75) Inventors: János Fischer, Budapest (HU); Tamás Fodor, Budapest (HU); Ferenc Trischler, deceased, late of Budapest (HU); by Ferenc Trischler, Jr., legal representative, Budapest (HU); by Tamás Róbert Trischler, legal representative, Budapest (HU); by Gabriel Maria Trischler, legal representative, Frankfurt-am-Main (DE); Sándor Lévai, Biatorbágy (HU); Endréne Petényi, Budapest (HU)

(73) Assignee: Richter Gedeon Vegyészeti Gyár RT., Budapest (HU)

( * ) Notice: Subject to any disclaimer, the term of this patent is extended or adjusted under 35 U.S.C. 154(b) by 384 days.

(21) Appl. No.: 10/432,387

(22) PCT Filed: Nov. 14, 2001

(86) PCT No.: PCT/HU01/00111

§ 371 (c)(1),
(2), (4) Date: Oct. 29, 2003

(87) PCT Pub. No.: WO02/42290

PCT Pub. Date: May 30, 2002

(65) Prior Publication Data

US 2005/0203116 A1    Sep. 15, 2005

(30) Foreign Application Priority Data

Nov. 23, 2000    (HU) .................................. 0004701

(51) Int. Cl.
C07D 221/06    (2006.01)
A61K 31/4465    (2006.01)

(52) U.S. Cl. ........................................ 546/79; 514/290
(58) Field of Classification Search ............... 546/79; 514/290
See application file for complete search history.

(56) References Cited

U.S. PATENT DOCUMENTS 4,282,233 A    8/1981    Vilani 4,659,716 A * 4/1987 Villani et al. ............... 514/290

FOREIGN PATENT DOCUMENTS

EP    152 897    8/1985

OTHER PUBLICATIONS

Berge et al., "Pharmaceutical Salts", Journal of Pharmaceutical Sciences, vol. 66, No. 1, pp. 1-19, 1977.*
Harris, D., Quantitative Chemical Analysis, Fifth Edition, pp. 230, and AP24 and AP25 of Appendix G, 1999.*

* cited by examiner

Primary Examiner—Rita Desai
(74) Attorney, Agent, or Firm—Hahn & Voight PLLC

(57) ABSTRACT

The object of the present invention are new desloratadine salts of formula I wherein the meaning of X is an acid residue and the meaning of n is 1 or 2, and formula II wherein the meaning of X is a pK <3.5 acid residue. The invention is related to a process for their synthesis, as well as new anti-allergic pharmaceutical compositions containing these salts

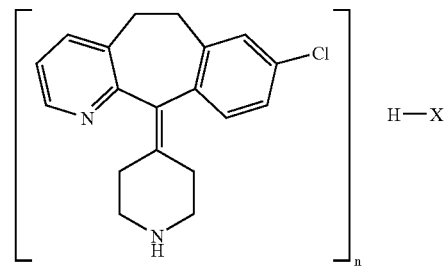

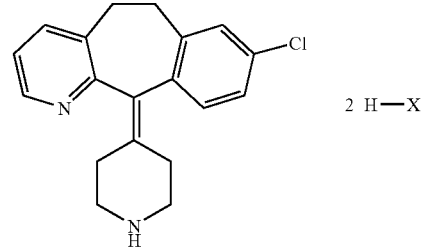

5 Claims, No Drawings

DESLORATADINE SALTS, PROCESS FOR THEIR SYNTHESIS AND PHARMACEUTICAL COMPOSITIONS THEREOF

The invention relates to new desloratadine salts, process for their synthesis, as well as new anti-allergic pharmaceutical compositions containing these salts.

It is known, that desloratadine (it's chemical name: 8-chloro-6,11-dihydro-11-(4-piperidilydene)-5H-benzo[5,6]cyclohepta[1,2-b]pyridine) is an active metabolite of a successful anti-allergic drug substance, loratadine. According to the literature desloratadine is 2.5–4 times more active orally than loratidine and antihistaminic activity lasts for 24 h (Arzneim. Forsch./Drug Res. 50 (I), Nr. 4 (345–352) 2000).

It is known from the Hungarian patent Number 194 864, that desloratadine base can be obtained from loratadine (chemical name: 8-chloro-6,11-dihydro-11-(1-ethoxycarbonyl-4-piperidilydene)-5H-benzo[5,6]cyclohepta[1,2-b]pyridine) by two methods. These are as follows:

a) the 8-chloro-6,11-dihydro-11-(1-ethoxycarbonyl-4-piperidilydene)-5H-benzo [5,6]cyclohepta[1,2-b]pyridine (loratadine) is decarbethoxylated by boiling with aqueous ethanolic sodium hydroxide solution for 24 h, then isolating the desloratadine acetate after neutralizing the solution with acetic acid. This crude product has to be further purified; the desloratadine acetate—according to the paper—is obtained in 70% yield after recrystallization from benzene-hexane mixture. The desloratadine base is prepared by basic treatment of desloratadine acetate and this is purified by recrystallization from hexane.

b) the 8-chloro6,11-dihydro-11-(1-methyl-4-piperidilydene)-5H-benzo[5,6]cyclohepta[1,2-b]pyridine is demethylated in two steps: first the 1-cyano-derivative is synthesized with cyanogen bromide and this is hydrolyzed with concentrated hydrochloric acid solution in acetic acid for 20 h, then after evaporating the solvents the residue is neutralized with ammonium hydroxide solution to obtain the desloratadine, the melting point of which is 149–151° C.

It is mentioned in the above Hungarian patent, that salts can be formed from desloratadine with pharmaceutically acceptable acids: hydrochloric: acid, methanesulfonic acid, sulfuric acid, acetic acid, maleinic acid, fumaric acid, phosphoric acid, but the formula, the physical- and physicochemical data and the method of their synthesis—except the above acetate salt—are not given.

The above mentioned processes for the synthesis of desloratadine have several disadvantages. During the realization of process a) substantial decomposition takes place, therefore, there are several impurities in the final product. The desloratadine base of required purity can be obtained by recrystallization, but this process can be carried out only with substantial loss of material. During the formulation of the active ingredient considerable disadvantage is from the point of technology, that the desloratadine base is insoluble in water.

Process b) is disadvantageous in itself, because of the use of poisonous cyanogen bromide reagent and the poisonous methyl bromide formed in the two-step reaction. On the other hand, the desloratadine base obtained by the latter method has the same disadvantages as the one obtained by method a).

In our experiments surprisingly we found that desloratadine acid addition salts of formula I

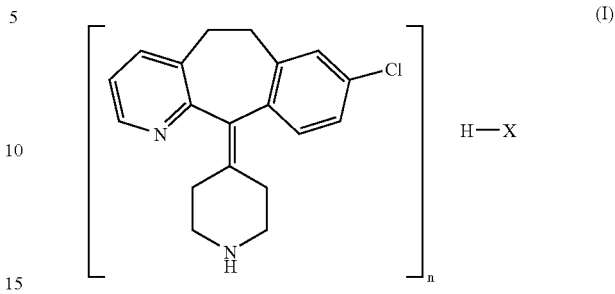

(I)

wherein the meaning of X is halogen atom, preferably chlorine or bromine, or acid residue, the meaning of n is 1 or 2, can be obtained by treatment/heating of loratadine base of formula III with certain acids.

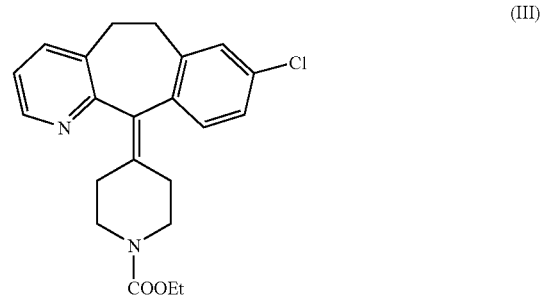

(III)

The so obtained acid addition salts are new and among them the desloratadine hemisulfate is particularly advantageous, because it can be obtained in one step, in high purity and stability. The other properties of the new acid addition salts are also favorable, for example their good solubility is advantageous from the point of drug formulation.

According to the above mentioned facts the invention relates to acid addition salts of formula I—wherein the meaning of X is an acid residue and the meaning of n is 1 or 2—as well as the acid addition salts of formula II

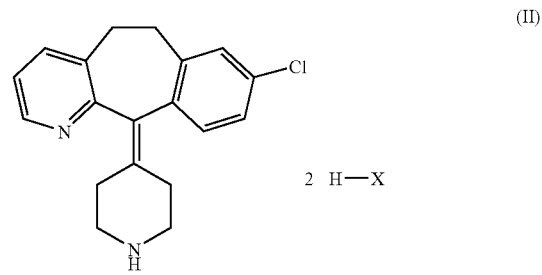

(II)

—wherein the meaning of X is an acid residue of pK<3.5 acid.

The invention also relates to the synthesis of acid addition salts of formula II, by reacting the loratadine of formula III (chemical name: 8-chloro-6,11-dihydro-11-(1-ethoxycarbonyl-4-piperidilydene)-5H-benzo[5,6]cyclohepta[1,2-b]pyridine) with concentrated mineral acid.

Further object of the invention is the method for the synthesis of acid addition salts of formula I—wherein the meaning of X is an acid residue and the meaning of n is 1 or 2—by treating an acid addition salt of formula II—wherein the meaning of X is an acid residue of pK<3.5 acid—or an aqueous solution of it with a solution of a base to adjust the pH to 6.5–7, then isolating the product.

Finally the invention relates to anti-allergic pharmaceutical composition containing 0.1–99.9% of active ingredient of formula I or II and 0.1–99.9% of pharmaceutically acceptable carriers and additives.

DETAILED DESCRIPTION OF THE PROCESS

In the process according to our invention the loratadine is heated with concentrated mineral acids, this way the urethane is hydrolyzed in a few hours and the salt of desloratadine formed with two mole acid (see formula 11, wherein the meaning of X is as given above) can be isolated in good yield.

According to a preferred realization of the invention the loratadine is heated with 60–80 wt. % sulfuric acid solution at 110–120° C., this way the hydrolysis of the urethane takes 3–6 h. The desloratadine disulfate can be isolated from the reaction mixture in good yield (80–95%).

According to an other preferred realization of the invention the loratadine is heated with concentrated hydrochloric acid at 115° C., this way the hydrolysis of the urethane takes 6 h and the desloratadine dihydrogen chloride salt can be isolated from the reaction mixture in high yield (90–95%).

According to a further realization of the invention the loratadine is heated with 48% hydrogen bromide solution at 110° C. This way the urethane is hydrolyzed in 6 h and the desloratadine dihydrogen bromide salt can be isolated in high yield (>95%).

The desloratadine double salts can be isolated not only in good yield, but in high purity as well.

According to our invention the desloratadine double salts can be transformed into simple salts with strong base.

Especially preferred the formation of desloratadine hemisulfate from desloratadine disulfate with addition of strong base, for example 25% tetramethylammonium hydroxide solution, to adjust the pH to 6.8 and isolating. the desloratadine hemisulfate.

The new desloratadine hemisulfate of our invention can be the active ingredient of a new, non-sedative H1-antagonist pharmaceutical composition.

The starting material of the compounds of the invention is loratadine (chemical name: 8-chloro-6,11-dihydro-11-(1-ethoxycarbonyl-4-piperidilydene)-5H-benzo[5,6]cyclohepta[1,2-b]pyridine). The synthesis of loratadine is described in detail in the U.S. Pat. No. 4,282,233 (the equivalent of which is the Hungarian patent Number 186 774).

The invention is illustrated by the following not limiting Examples:

Example 1

Desloratadine Disulfate

A mixture of 19.5 g (50 mmol) of loratadine and 40 g of 72 wt. % sulfuric acid is stirred at 115° C. for 6 h. The reaction mixture is cooled to room temperature, 100 ml of methanol is added, then the mixture is cooled to 0° C. and stirred at this temperature for 3 h. The precipitated crystalline product is filtered off, washed with ice-cold methanol. After drying 20.95 g (84%) of the title compound is obtained. Melting point: 244–246° C.

According to HPLC measurements the purity of the product is >99.5%.

Determination by Titrimetry:

The desloratadine disulfate is dissolved in 80% acetone and it is titrated with 0.1 N sodium hydroxide solution by potentiometry. The titration curve has two inflection points; the two bisulfate anion and the proton on the nitrogen of the pyridine are titrated till the first inflection point and the proton on the nitrogen of the piperidine is titrated between the two inflections. The ratio of the two area is 3/1.

Example 2

Desloratadine Dihydrogen Chloride

A mixture of 5.0 g (13 mmol) of loratadine (in solid form) and 50 ml of concentrated hydrochloric acid is stirred at 115° C. for 6 h. The excess of hydrochloric acid is evaporated and the residue is crystallized with 30 ml of acetone. The crystalline suspension is stirred at 0° C. for 5 h, filtered and washed with acetone to yield 4.7 g (94%) of the title compound. Melting point: 210–220° C.

Example 3

Desloratadine Dihydrogen Bromide

A mixture of 3.83 g (10 mmol) of loratadine and 30 ml of 48% hydrogen bromide is stirred at 115° C. for 6 h. The excess of hydrogen bromide is evaporated and the residue is dissolved in 20 ml of hot ethanol. The title compound is precipitated in crystalline form after cooling. The crystalline suspension is stirred at 0° C. for 3 h, filtered and washed with ice-cold ethanol to yield 4.7 g (99%) of the title compound. Melting point: 247–250° C.

Example 4

Desloratadine Hemisulfate 3.04 g (6 mmol) of desloratadine disulfate (obtained according to Example 1) is dissolved in a mixture of 5 ml of water and 2 ml of ethanol, then cooled to 0° C. and the pH is adjusted to 6.8 with addition of 25% tetramethylammonium hydroxide solution. The solvent is evaporated and the residue is stirred with 50 ml of ethanol at 0° C. for 5 h, filtered and washed with ice-cold ethanol to yield 1.64 g (76%) of the title compound. Melting point: 279–280° C.

Determination by Titrimetry:

The desloratadine hemisulfate is dissolved in 80% acetone and it is titrated with 0.1 N sodium hydroxide solution by potentiometry. Only one inflection point is observed, which is equivalent with the proton on the nitrogen of the piperidine.

Example 5

General Procedure for the Preparation of Salts of Formula I 5.07 g (10 mmol) of desloratadine disulfate is suspended in 50 ml of dichloromethane and 10 ml of 4N sodium hydroxide solution is added. After vigorous stirring the solutions clear up. The organic layer is separated, washed with 10 ml of saturated sodium chloride solution and dried over anhydrous magnesium sulfate. 10 mmol of acid of formula HX is added to the dichloromethane solution. The product is precipitated from the solution in crystalline form after cooling.

The following salts of formula I were prepared:

| n | X | Melting point (° C.) | pH of 1% solution | $H_2O$ | Yield (%) |
|---|---|---|---|---|---|
| 1 | $C_6H_5$—$SO_3$ | 212–214 | 5.6 | 0 | 91 |
| 1 | $CH_2$—COOH<br>\|<br>HO—C—COOH<br>\|<br>$CH_2$—COOH | 63–114 | 4.5 | 2 | 95 |
| 1 | COO<br>\|<br>CH—OH<br>\|<br>CH—OH<br>\|<br>COOH | 183 | 4.2 | 2 | 99 |
| 1 | $CH_3$—$SO_3$ | 242–247 | 5.2 | 0 | 95 |
| 1 | $HSO_4$ | 237–247 | 3.0 | 0 | 88 |
| 1 | Cl | 271–273 | 4.8 | 0 | 77 |
| 1 | CH—COOH<br>\|\|<br>CH—COO | 169–171 | 5.0 | 0 | 94 |

Example 6

Preparation of a Pharmaceutical Composition

For 100 mg tablets the following ingredients are required (for one tablet):

| desloratadine hemisulfate (prepared according to Example 4) | 5.0 mg |
| lactose | 47.0 mg |
| corn-starch | 47.0 mg |
| magnesium stearate | 1.0 mg |

The mixture of the powders is pressed into tablets directly after homogenization.

Example 7

Preparation of a Pharmaceutical Composition

For 100 mg tablets the following ingredients are required (for one tablet):

| desloratadine hemisulfate (prepared according to Example 4) | 5.0 mg |
| lactose | 25.0 mg |
| corn-starch | 69.0 mg |
| magnesium stearate | 1.0 mg |

The mixture of the powders is pressed into tablets directly after homogenization.

Example 8

Preparation of a Pharmaceutical Composition

For 100 mg tablets the following ingredients are required (for one tablet):

| desloratadine hemisulfate (prepared according to Example 4) | 5.0 mg |
| lactose | 69.0 mg |
| corn-starch | 25.0 mg |
| magnesium stearate | 1.0 mg |

The mixture of the powders is pressed into tablets directly after homogenization.

What is claim is:

1. A desloratadine hemisulfate of formula I

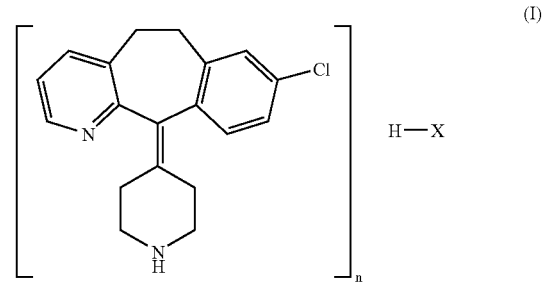

(I)

wherein X is a hydrogensulfate group and n is 2.

2. A process for the synthesis of acid addition salts of formula II,

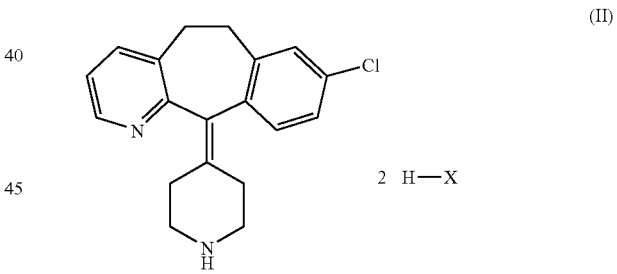

(II)

wherein X is a hydrogensulfate group,
said process comprising reacting a loratadine of formula III

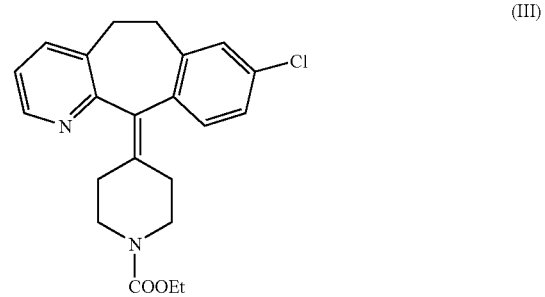

(III)

with concentrated sulfuric acid.

3. A process for the synthesis of a desloratadine hemisulfate of formula I

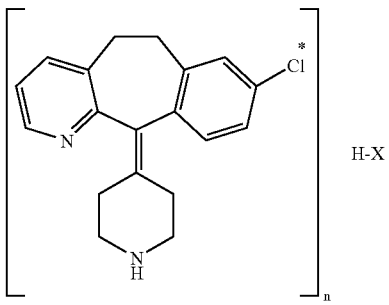

(I)

wherein X is a hydrogensulfate group and n is 2,
said process comprising treating a desloratadine salt of formula II

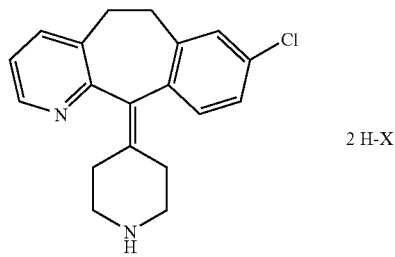

(II)

wherein X is a hydrogensulfate group, or the aqueous solution thereof, with a solution of a base to adjust the pH to 6.5–7 and isolating the product.

4. An anti-allergic pharmaceutical composition, comprising 0.1–99.9% of the desloratadine hemisulfate of formula I of claim 1 as active ingredient and 0.1–99.9% of pharmaceutically acceptable carriers and additives.

5. The process of claim 3, wherein the desloratadine salt of formula II is obtained by reacting the loratidine of formula III

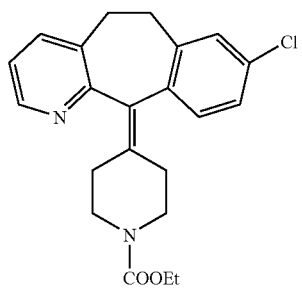

(III)

with concentrated sulfuric acid.

* * * * *